US011203753B2

(12) United States Patent
Peyssonnaux et al.

(10) Patent No.: US 11,203,753 B2
(45) Date of Patent: Dec. 21, 2021

(54) HEPCIDIN ANTAGONISTS FOR USE IN THE TREATMENT OF INFLAMMATION

(71) Applicants: INSERM (INSTITUT NATIONAL DE LA SANTE ET DE LA RECHERCHE MEDICALE), Paris (FR); CENTRE NATIONAL DE LA RECHERCHE SCIENTIFIQUE—CNRS, Paris (FR); UNIVERSITE PARIS DESCARTES, Paris (FR); UNIVERSITE PARIS DIDEROT—PARIS 7, Paris (FR)

(72) Inventors: Carole Peyssonnaux, Pairs (FR); Jacques Mathieu, Paris (FR); Sara Zumerle, Paris (FR)

(73) Assignees: INSERM (Institut National de la Santé et de la Recherche Médicale), Paris (FR); Centre National de la Recherche Scientifique (CNRS), Paris (FR); Université Paris Descartes, Paris (FR); Université Paris Diderot—Paris 7, Paris (FR)

(*) Notice: Subject to any disclaimer, the term of this patent is extended or adjusted under 35 U.S.C. 154(b) by 0 days.

(21) Appl. No.: 15/557,646

(22) PCT Filed: Mar. 14, 2016

(86) PCT No.: PCT/EP2016/055458
§ 371 (c)(1),
(2) Date: Sep. 12, 2017

(87) PCT Pub. No.: WO2016/146587
PCT Pub. Date: Sep. 22, 2016

(65) Prior Publication Data
US 2018/0057812 A1 Mar. 1, 2018

(30) Foreign Application Priority Data

Mar. 13, 2015 (EP) .................................... 15159033

(51) Int. Cl.
| C07K 16/26 | (2006.01) |
| A61K 9/00 | (2006.01) |
| C12N 15/113 | (2010.01) |
| A61K 31/713 | (2006.01) |
| A61K 31/7105 | (2006.01) |
| A61K 31/77 | (2006.01) |
| C12N 15/115 | (2010.01) |

(52) U.S. Cl.
CPC .......... *C12N 15/113* (2013.01); *A61K 31/713* (2013.01); *A61K 31/7105* (2013.01); *A61K 31/77* (2013.01); *C07K 16/26* (2013.01); *C12N 15/115* (2013.01); *A61K 9/0031* (2013.01); *C12N 2310/11* (2013.01); *C12N 2310/12* (2013.01); *C12N 2310/14* (2013.01); *C12N 2310/16* (2013.01); *C12N 2310/531* (2013.01)

(58) Field of Classification Search
None
See application file for complete search history.

(56) References Cited

U.S. PATENT DOCUMENTS

2003/0147890 A1* 8/2003 Ye

FOREIGN PATENT DOCUMENTS

| WO | WO 2005/070451 A1 * | 8/2005 |
| WO | 2008097461 | 8/2008 |
| WO | 2009139822 | 11/2009 |
| WO | 2014/152006 A2 | 9/2014 |

OTHER PUBLICATIONS

Dilek et al. (2014, Indian J. Dermatol. 59(6): 630 [9 pages]).*
Ashby et al. (2010, Haematologica 95(3):505-508).*
Terui et al. (2000, Exp. Dermatol. 9:1-10).*
Crosby et al., 2006, Blood 108(11, Part 1):83A-84A.*
Schwoebel et al., 2013, ZBlood 121(12):2311-2315.*
Eijk et al., 2014, Blood 124(17):2643-2646.*
E. Fung et al: "Manipulation of the hepcidin pathway for therapeutic purposes", Haematologica, vol. 98, No. 11, pp. 1667-1676, Nov. 1, 2013.
Eileen Fung et al: "Highthroughput screening of small molecules identifies hepcidin antagonists", Molecular Pharmacology, pp. 681-690 Mar. 1, 2013.
Konstantinos H Katsanos et al: "Recombinant human erythropoietin in patients with inflammatory bowel disease and refractory anemia: A 15-year single center experience", Journal of Chron's and Coitis, Elsevier BV, NL, vol. 6, No. 1, Jul. 8, 2011.
Sun et al., "Targeting the hepcidin-ferroportin axis to develop new treatment strategies for anemia of chronic disease and anemia of inflammation." American journal of hematology 87.4 (2012): 392-400.
Hsieh et al., "Silencing of hepcidin enforces the apoptosis in iron-induced human cardiomyocytes." Journal of Occupational Medicine and Toxicology 9.1 (2014): 11.
Isis Pharmaceuticals, "Xenon Licenses Antisense Drug XEN701 From Isis and Initiates Preclinical Toxicology Studies", Press Release, Jun. 10, 2013.
Poli et al., "Hepcidin antagonists for potential treatments of disorders with hepcidin excess", Frontiers in Pharmacology, Apr. 28, 2014, vol. 5, Article 86.
Theurl et al., "Pharmacologic inhibition of hepcidin expression reverses anemia of chronic inflammation in rats", Blood, The Journal of the American Society of Hematology 118.18 (2011): 4977-4984.

* cited by examiner

*Primary Examiner* — Elizabeth C. Kemmerer
(74) *Attorney, Agent, or Firm* — W&C IP

(57) ABSTRACT

The present invention relates to a hepcidin antagonist for use in the treatment of inflammatory diseases.

2 Claims, 10 Drawing Sheets

HEPCIDIN ANTAGONISTS FOR USE IN THE TREATMENT OF INFLAMMATION

FIELD OF THE INVENTION

The present invention relates to a hepcidin antagonist for use in the treatment of inflammatory diseases.

BACKGROUND OF THE INVENTION

Inflammation is the body's immediate response to damage to its tissues and cells by pathogens, noxious stimuli such as chemicals, or physical injury. (U. Weiss, Nature Insight, 2008, Vol. 454, Issue no. 7203). Though this phenomenon is extremely important for the accomplishment of healing processes, dysregulated inflammation can have severe consequences.

Inflammation can be divided into two forms: acute inflammation, which is a short term response, and chronic inflammation, which is a dysregulated and maladaptive reaction highly detrimental for the host. It is now well established that chronic inflammation is involved in the development of several diseases among which are cardiovascular diseases, obesity, diabetes, asthma, inflammatory bowel diseases, allergies and rheumatoid arthritis (Durgaprasad L. et al, Inflammation & Allergy-Drug Targets, 2013, 12, 349-361). Acute inflammation is considered as mainly beneficial in the healing process, but when it is uncontrolled, it can lead to severe pathologies as for example the Systemic Inflammatory Response Syndrome (SIRS) and sepsis which are both common causes of morbidity and death in intensive care units (Fitting C. et al, PloS one 7.6, 2012, e38916). Nonsteroidal anti-inflammatory (NSAIDs) are the most commonly used anti-inflammatory drugs but have several side effects among which are gastrointestinal ulcers and bleeding (H. Süleyman et al., Pharmacological Reports, 2007, 59, 247-258).

Thus, there is a continued need to develop novel drugs and therapies for treating inflammatory disorders.

The inventors of the present invention have discovered that, surprisingly, hepcidin which is also known as the iron homeostasis hormone, is able to stimulate inflammatory responses and that accordingly, it would represent a promising target in the treatment of inflammatory reaction.

SUMMARY OF THE INVENTION

Hepatic hepcidin is known as being the key hormone in iron homeostasis; it is able to decrease plasma iron levels by blocking iron absorption in the duodenum and iron release from macrophages thus targeting the two entrance gates for iron in the circulation. Several stimuli have been shown to be involved in hepcidin regulation: iron, hypoxia, erythropoietic demand and inflammation.

The present invention relies on the discovery that, surprisingly, when it is produced locally, hepcidin is able to directly initiate inflammation by triggering the recruitment of neutrophils and the pro-inflammatory responses of macrophages. Hepcidin therefore constitutes a promising new target for treating inflammatory diseases.

Thus the present invention relates to a hepcidin antagonist for use in the treatment of an inflammatory disease.

DETAILED DESCRIPTION

Hepcidin was first identified as a liver-derived antimicrobial peptide. The human hepcidin gene encodes an 84-residue prepropeptide that contains a 24-residue N-terminal signal peptide that is subsequently cleaved to produce pro-hepcidin. Pro-hepcidin is then processed to produce a mature 25-amino acid hepcidin (Jordan et al., The Journal of Biological chemistry, 2009, 284, 36, 24155-24167).

It is now well established that hepatic hepcidin is the regulator of iron homeostasis (as disclosed by Lesbordes-Brion et al., Blood, 2006, 108, 1402-1405 and Nicolas et al., Proc. Natl. Acad. Sci. U.S.A., 2002, 99, 4596-4601). Hepcidin is a hypoferremic hormone; it binds to and degrade ferroportin (FPN, the only iron exporter known to date), thereby decreasing the iron levels in the circulation.

Since its expression can be induced by inflammation (Nicolas et al., J. Clin. Invest., 2002, 110, 1037-1044), hepcidin has been proposed as an important mediator of Anemia of Chronic disease (ACD), also known as Anemia of Inflammation (AI). ACD patients have increased hepcidin levels and cannot be treated with oral iron, since the metal is inefficiently absorbed. For these reasons, hepcidin antagonists have been proposed and are largely described for the treatment of ACD (Ruchala and Nemeth, Trends Pharmacol., 2002, Sci. 35, 155-161; Sun et al., 2012, Am. J. Hematol. 87, 392-400).

The inventors have demonstrated that hepcidin promotes direct neutrophil migration and indirect neutrophil migration through macrophage-induced specific neutrophil chemoattractants such as CXCL1 and CXCL2, and, at high concentrations, stimulates IL-beta, TNF-alpha and NOS2 expression in macrophages thereby acting as a pro-inflammatory molecule. The inventors have further demonstrated that an inhibition of hepcidin in the intestine blunted the effects of the inflammation due to a lipopolysaccharide injection (LPS).

Thus, the present invention relates to a hepcidin antagonist for use in the treatment of an inflammatory disease.

According to the invention, a "hepcidin antagonist" refers to a compound which is an inhibitor of the hepcidin expression or hepcidin activity. In a particular embodiment, the hepcidin antagonist inhibits the human mature 25-amino acid hepcidin.

As used herein, the terms "treating" or treatment" relates to reversing, alleviating, inhibiting the progress of, or preventing the disorder or condition to which such term applies, or reversing, alleviating, inhibiting the progress of, or preventing one or more symptoms of the disorder or condition to which such term applies.

As used herein, the terms "inflammatory disease" or "inflammatory disorder" relates to a complex reaction of vascularized tissue to infection, toxin exposure, or cell injury that involves extravascular accumulation of plasma proteins and leukocytes (Abbas et al., Cellular and Molecular Immunology, $7^{th}$ edition, 2011).

Inflammatory diseases can be divided into to two groups: acute inflammatory diseases and chronic inflammatory diseases.

By "acute inflammatory diseases" it is herein referred to a common result of innate immune responses, and local adaptive immune responses. Acute inflammation is the initial response of the body to harmful stimuli and is achieved by the increased movement of plasma and leukocytes from the blood into the injured tissues. Although inflammation serves a protective function in controlling infections and promoting tissue repair, it can also cause tissue damage and disease (Abbas et al., Cellular and Molecular Immunology, $7^{th}$ edition, 2011). Examples of acute inflammatory diseases are Systemic Inflammatory Response Syndrome (SIRS), sepsis, peritonitis, reperfusion injury, pancreatitis, nephritis, myocarditis, encephalitis, pelvic inflammatory disease, vasculitis, uveitis, keratitis and acne vulgaris.

By "chronic inflammatory diseases" it is herein referred to prolonged inflammation that leads to a progressive shift in the type of cells present at the site of inflammation and is characterized by simultaneous destruction and healing of the tissue from the inflammatory process. Examples of chronic inflammatory diseases are Inflammatory Bowel Diseases (IBD) as Crohn's disease and ulcerative colitis, celiac disease, chronic bronchitis, chronic obstructive pulmonary disease, chronic prostatitis, gastritis, atherosclerosis, rheumatoid arthritis, obesity, allergies, asthma, psoriasis, dermatitis, eczema.

In another embodiment, the present invention relates to a hepcidin antagonist for use in the treatment of an inflammatory disease, wherein said inflammatory disease is an acute inflammatory disease.

In another embodiment, the present invention relates to a hepcidin antagonist for use in the treatment of an inflammatory disease, wherein said inflammatory disease is a chronic inflammatory disease.

In a particular embodiment, the present invention relates to a hepcidin antagonist for use in the treatment of an inflammatory disease, wherein said inflammatory disease is an autoimmune disease.

By "autoimmune diseases", it is herein referred to conditions characterized by an abnormal immune response of the body against substances and tissues normally present in the body.

In another particular embodiment, the present invention relates to a hepcidin antagonist for use in the treatment of an inflammatory disease, wherein said inflammatory disease is an auto-inflammatory disease.

By "auto-inflammatory diseases", it is herein referred to a group of conditions characterized by recurrent episodes of systemic and organ-specific inflammation without apparent involvement of antigen-specific T cells or significant production of auto-antibodies.

In a further embodiment, the present invention relates to a hepcidin antagonist for use in the treatment of an inflammatory disease, wherein said inflammatory disease is a host-versus-graft disease.

By "host-versus-graft disease", it is herein referred to a complication following an allogenic transplant wherein the grafted tissue cells attack the host cells.

In a particular embodiment, the inflammatory disease according to the invention is not linked to an infectious disease.

By "non-infectious disease", it is referred to a disease which is not caused by pathogenic microorganisms, such as bacteria, viruses, parasites or fungi.

As stated above, hepcidin antagonists have already been largely disclosed in the prior art (see for example Fung and Nemeth, Haematologica, 2013, 98, 1667-1676) and one skilled in the art would easily produce them.

Hepcidin Antagonists

Inhibitors of the Hepcidin Expression

A first object of the present invention relates to a hepcidin antagonist which is an inhibitor of the hepcidin expression for use in the treatment of an inflammatory disease.

By "inhibitor of the hepcidin expression", it is herein referred to a compound which is capable of reducing or suppressing the synthesis of functional hepcidin.

In one embodiment, the compound according to the invention can be an erythropoiesis-stimulating agent like erythropoietin (see Ashby et al., Haematologica, 2010, 95(3), 505-8).

Small inhibitory RNAs (siRNAs) can also function as inhibitors of hepcidin gene expression for use in the present invention. Hepcidin gene expression can be reduced by contacting a subject or cell with a small double stranded RNA (dsRNA), or a vector or construct causing the production of a small double stranded RNA, such that hepcidin gene expression is specifically inhibited (i.e. RNA interference or RNAi). Methods for selecting an appropriate dsRNA or dsRNA-encoding vector are well known in the art for genes whose sequence is known (e.g. see for example Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of hepcidin gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of hepcidin mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of hepcidin gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing hepcidin. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, eye, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In a preferred embodiment, the antisense oligonucleotide, siRNA, shRNA or ribozyme nucleic acid sequence is under the control of a heterologous regulatory region, e.g., a heterologous promoter.

Inhibitors of the Hepcidin Activity

A second aspect of the present invention relates to a hepcidin antagonist which is an inhibitor of the hepcidin activity for use in the treatment of an inflammatory disease.

By "inhibitor of the hepcidin activity", it is herein referred to a compound which is capable of reducing or suppressing the inflammatory activity of hepcidin. In view of the teaching of the present disclosure, particularly of the examples, it falls within the ability of the skilled person to assess whether a compound is an inhibitor of the hepcidin activity. For example, a suitable test consists in evaluating if said compound inhibits the chemoattractant effect of hepcidin on neutrophils i.e. hepcidin-induced neutrophil migration. A suitable test for detecting hepcidin-induced neutrophil migration is described in examples hereinafter.

In a particular embodiment, the present invention relates to a compound which is an inhibitor of the hepcidin activity for use in the treatment of inflammatory diseases, wherein said compound is an anti-hepcidin antibody which neutralizes hepcidin (see for example Cooke et al., Blood, 2013, 122(17); Sasu et al., Blood, 2010, 115(17), 3616-24; U.S. Pat. No. 8,629,250; WO2009058797; WO2010017070; WO2009139822; WO2014152006) or an anti-hepcidin antibody fragment which neutralizes hepcidin.

Antibodies directed against hepcidin can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against hepcidin can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g., U.S. Pat. No. 4,946,778) can be adapted to produce anti-hepcidin single chain antibodies. Hepcidin activity inhibitors useful in practicing the present invention also include anti-hepcidin antibody fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to hepcidin.

Humanized anti-hepcidin antibodies and antibody fragments therefrom can also be prepared according to known techniques. "Humanized antibodies" are forms of non-human (e.g., rodent) chimeric antibodies that contain minimal sequence derived from non-human immunoglobulin. For the most part, humanized antibodies are human immunoglobulins (recipient antibody) in which residues from a hypervariable region (CDRs) of the recipient are replaced by residues from a hypervariable region of a non-human species (donor antibody) such as mouse, rat, rabbit or nonhuman primate having the desired specificity, affinity and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. Methods for making humanized antibodies are described, for example, by Winter (U.S. Pat. No. 5,225,539) and Boss (Celltech, U.S. Pat. No. 4,816,397).

Then, for this invention, neutralizing antibodies of hepcidin are selected.

In still another embodiment, hepcidin activity inhibitors may be selected from aptamers. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

Then, for this invention, neutralizing aptamers of hepcidin are selected.

In a particular embodiment, the compound according to the invention is an anti-hepcidin Spiegelmer® like lexaptepid pegol (NOX-H94) (see Schwoebel et al., Blood, 2013, 121(12), 2311-2315; WO2012055573; WO2010124874) which is produced by NOXXON and currently tested in phase II trials.

In a further embodiment, the compound according to the invention is an Anticalin® that binds to hepcidin like PRS-080 (see Hohlbaum et al., Am J Hematol., 2013, 5(88), E41; WO2012022742) which is produced by PIERIS AG and currently tested in phase I trials. General methods for producing anticalins are for example described in WO9916873.

Another object of the invention is a method for treating an inflammatory disorder comprising administering to a subject in need thereof a therapeutically effective amount of a hepcidin antagonist as disclosed above.

By a "therapeutically effective amount" is meant a sufficient amount of compound to treat and/or to prevent the inflammatory disorder.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

The hepcidin antagonist according to the invention can be administered by any suitable route of administration. For example, the antagonist according to the invention can be administered by oral (including buccal and sublingual), rectal, nasal, topical, pulmonary, vaginal, or parenteral (including intramuscular, intra-arterial, intrathecal, subcutaneous and intravenous) administration or in a form suitable for administration by inhalation or insufflation.

The antagonists of the present invention, together with one or more conventional adjuvants, carriers, or diluents may be placed into the form of pharmaceutical compositions and unit dosages. The pharmaceutical compositions and unit dosage forms may comprise conventional ingredients in conventional proportions, with or without additional active compounds or principles, and the unit dosage forms may contain any suitable effective amount of the active ingredients commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal administration; or in the form of sterile injectable solutions for parenteral uses. Formulations containing about one (1) milligram of active ingredient or, more broadly, about 0.01 to about one hundred (100) milligrams, per tablet, are accordingly suitable representative unit dosage forms.

The antagonists of the present invention may be formulated in a wide variety of oral administration dosage forms. The pharmaceutical compositions and dosage forms may comprise compounds of the present invention or pharmaceutically acceptable salts thereof as the active component. The pharmaceutically acceptable carriers may be either solid or liquid. Solid form preparations include powders, tablets, pulls, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired.

The powders and tablets preferably contain from about one (1) to about seventy (70) percent of the active compound. Suitable carriers include but are not limited to magnesium carbonate, magnesium stearate, talc, sugar, lactose, pectin, dextrin, starch gelatin, tragacanth, methylcellulose sodium carboxymethylcellulose, a low melting wax, cocoa butter, and the like.

The term "preparation" is intended to include the formulation of the active compound with an encapsulating material as carrier, providing a capsule in which the active component, with or without carriers, is surrounded by a carrier, which is in association with it. Similarly, cachets and lozenges are included. Tablets, powders, capsules, pulls, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavours, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilising agents, and the like.

The antagonists of the present invention may be formulated for administration as suppositories. Typically, a low melting wax, such as a mixture of fatty-acid glycerides or cocoa butter is first melted and the active component is dispersed homogeneously.

The antagonists of the present invention may be formulated for parenteral administration (e.g., by injection, for example bolus injection or continuous infusion) and may be presented in unit dose form in ampoules, pre-filled syringes small volume infusion or in multi-dose containers with an added preservative. The compositions may take such forms as suspensions, solutions, or emulsions in oily or aqueous vehicles, for example solutions in aqueous polyethylene glycol. Examples of oily or non-aqueous carriers, diluents solvents or vehicles include propylene glycol, polyethylene glycol, vegetable oils (e.g., olive oil, and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The antagonists of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier. Formulations suitable for topical administration to the eye include eye drops wherein the active ingredient is suspended or dissolved in a suitable carrier, preferably an aqueous solvent.

The antagonists according to the present invention may be formulated for intrapulmonary administration. Suitable formulations for intrapulmonary applications have a particle size typically in the range of 0.1 to 500 microns and are administered by inhalation through the nasal tract or through the mouth in the form of a dry powder or via an aerosol.

Applications According to the Invention

The present inventors have more specifically discovered that intestinal hepcidin plays a major role in intestinal and systemic inflammation. Intestinal hepcidin is dramatically increased in mice having received an intraperitoneal injection of LPS, whereas hepatic hepcidin is only moderately induced. LPS injection is a classic model of systemic inflammation (Andreansen et al, Current Medicinal Chemistry, 2008, 15, 17, 1697-1705(9)).

In their results, the inventors have observed that hepcidin acts as an intestinal chemokine to trigger neutrophil infiltration and macrophage activation in the lamina propria during systemic inflammation. These results prove that hepcidin can act as a pro-inflammatory agent and allow the expression of several inflammation mediators (such as IL-1beta, TNF-alpha and NOS2).

Furthermore, the inventors have observed that a specific inhibition of intestinal hepcidin prevents the production of several pro-inflammatory agents normally observed after LPS injection. Intestinal hepcidin is thus critically required for triggering systemic inflammation upon LPS stimulation. Since an inhibition of intestinal hepcidin strikingly reduces the effects of LPS injection (mimicking systemic inflammation), it is here proposed that local inhibition of hepcidin can have a protective effect against inflammation.

In view of the above, a local inhibition of intestinal hepcidin would represent a very promising way to treat inflammatory disorders, particularly those triggering intestinal inflammation.

Regarding the fact that:
the gut is considered as the motor of the systemic inflammatory response (Mittal, R. & Coopersmith, C. M. Redefining the gut as the motor of critical illness. *Trends Mol Med* 20, 214-223 (2014)); and
hepcidin inhibition protects from the effects of systemic inflammation;

it is herein proposed that a hepcidin inhibition would be beneficial for treating systemic inflammatory responses. The main systemic inflammation disorders are SIRS, sepsis or peritonitis.

Accordingly, it is herein provided a hepcidin antagonist for use in the treatment of inflammatory diseases, wherein said inflammatory is selected from the group consisting of SIRS, sepsis or peritonitis.

In view of the above, it is further proposed that local inhibition of intestinal hepcidin would prevent local inflammation observed in the inflammatory diseases of the intestinal tract. Among all the inflammatory disorders directly involving an inflammation of the intestinal tract, the most important are the inflammatory bowel diseases. Crohn's disease and ulcerative colitis are the main IBD.

Thus, in a particular embodiment, the present invention relates to a hepcidin antagonist for use in the treatment of an inflammatory disease, wherein said inflammatory disease is an IBD.

In a further embodiment the present invention discloses an antagonist of hepcidin for use in the treatment of an IBD, wherein said IBD is selected from Crohn's disease and ulcerative colitis.

In order to be administered specifically to the intestines, the hepcidin antagonist can be administered orally or rectally.

When administered orally, the compound according to the invention can be in the form of a sustained release composition so as to deliver the compound to the intestines.

Thus, in a preferred embodiment, the present invention relates to a hepcidin antagonist for the treatment of an inflammatory disease selected from the group consisting of SIRS, sepsis, peritonitis, Crohn's disease and ulcerative colitis, wherein said compound is administered orally or rectally.

Although its main source is liver, numerous studies have demonstrated that pancreas, kidney, adipose tissue, heart, brain, eye, lungs and epidermis are also able to express hepcidin.

By analogy to the results disclosed herein-before, it is proposed that an inhibition of the hepcidin produced by a specific organ would allow treating inflammatory diseases affecting said organ.

Epidermis

Epidermis is subject to a lot of disorders involving unregulated inflammatory responses among which are eczema, psoriasis dermatitis and contact allergies. All these pathologies involve the recruitment of inflammatory mediators in the skin.

Thus, the present invention provides a hepcidin antagonist for use in the treatment of an inflammatory disease selected from the group consisting of psoriasis, dermatitis, eczema and contact allergy. In order to be directly administered to the skin, the hepcidin antagonist can be administered topically to the skin.

Eye

The expression of hepcidin in the eye is disclosed by Gnana et al (Gnana et al., Biochem. J., 2008, 411,79). They have demonstrated that intravitreal injection of LPS induces hepcidin expression in the retina. The main inflammatory disorders affecting the eye are uveitis and keratitis.

Following the same line of reasoning as before, it is herein proposed that a local inhibition of the eye-produced hepcidin would allow treating eye-inflammatory disorders such as uveitis and keratitis.

Accordingly, the present invention provides a hepcidin antagonist for use in the treatment of an inflammatory disease selected from uveitis and keratitis.

In order to administrate the hepcidin antagonist specifically to the eye, the antagonist according to the invention can be administered by intraocular injection or by topical administration to the eye.

Pancreas, Kidney, Heart and Vascular Tissues

Hepcidin is expressed in the pancreas (Krijt et al., J. Hepatol., 2004, 40, 891-896), in the kidney (Kulaksiz et al., J. Endocrinol., 2005, 184, 361-370), in the heart (Isoda et al., J. Nutr. Biochem., 2010, 21, 749-756), and in the vascular tissues (Raha et al., 2013, Acta Neuropathologica Comm., 1:55).

Pancreatic hepcidin expression is induced by intraperitoneal LPS injection, as observed by Krijt et al. Hepcidin is also induced in the heart by systemic inflammation (Merle et al., Endocrinology, 2007, 148, 2663-2668) and overexpressed in rat cardiomyocytes after experimental autoimmune myocarditis (Isoda et al., J. Nutr. Biochem., 2010, 21, 749-756).

Thus, according to the present invention, an inhibition of hepcidin in said organs would allow treating inflammatory diseases directly affecting these organs.

Accordingly, in a particular embodiment, the present invention relates to a hepcidin antagonist for use in the treatment of an inflammatory disease selected from the group consisting of pancreatitis, nephritis, myocarditis and atherosclerosis.

In that case, the antagonist according to the invention would be administered systemically.

Adipose Tissue

Adipose tissue expresses hepcidin (Bekri et al., Gastroenterology, 2006, 131, 788-796). During obesity, a macrophage infiltration in the adipose tissues resulting in an inflammation of said tissue is observed (Wellen et al., J Clin Invest., 2003, 112(12), 1785-1788.). It is herein proposed that a local inhibition of hepcidin in the adipose tissues would be beneficial in the treatment of obesity.

Thus, in a particular embodiment, the present invention relates to hepcidin antagonist for use in the treatment of obesity.

In this case, the antagonist according to the invention would be administered by a subcutaneous injection into the adipose tissue.

Lung

Hepcidin expression by lung cells has been disclosed by Frazier et al (Frazier et al., Respir. Res., 2011, 12, 100). Lungs are affected by several inflammatory diseases among which are asthma, chronic obstructive pulmonary disease and chronic bronchitis. Bronchial epithelial cells express hepcidin and induce it if stimulated in vitro by IL-6 or IFN-γ (Frazier et al., Respir. Res. 2011, 12, 100). Thus the present invention provides a compound, which is hepcidin antagonist for use in the treatment of an inflammatory disease selected from the group consisting of asthma, chronic obstructive pulmonary disease and chronic bronchitis.

In that case, the antagonist according to the invention would be administered by any method allowing the specific targeting of the lungs such as inhaling or spray drying for instance.

Brain

Hepcidin is also expressed in several region of the brain (Hänninen et al., BMC Neurosci., 2009, 10, 36). The inflammation of the brain tissue is the encephalitis. Multiple sclerosis (MS) is also an inflammatory disease in which the insulating covers of nerve cells in the brain and spinal cord are damaged.

In rats, both systemic and intracerebroventricular injections of LPS induce hepcidin expression in the cortex and in the substantia nigra (Qian et al., Mol. Neurobiol. 2014, 50(3):811-20; Wang et al., Endocrinology. 2008, 149(8): 3920-5).

In a further embodiment, the present invention thus provides a hepcidin antagonist for use in the treatment of encephalitis and MS.

In that case, any route of administration allowing the compound to reach the brain would be chosen. For example, in that case, the antagonist according to the invention would be administered by intrathecal or intraventricular injection.

Synovial Membrane

As disclosed in Nieuwenhuizen et al (Nieuwenhuizen et al., Haemophilia. 2013, 19(4), 218-27), human synovium also expresses hepcidin. Proinflammatory cytokines, such as IL-1beta and TNF-alpha are known to be correlated with rheumatoid arthritis disease activity. Rheumatoid arthritis being the major inflammatory disease affecting the synovial tissue, the present invention provides a hepcidin antagonist for use in the treatment of rheumatoid arthritis.

In this case, the antagonist according to the invention would be administered by subcutaneous or intra-articular injection.

Cytokines levels measured in the plasma of WT (black square) and Hepc$^{\Delta int}$ (open square) mice (n=10) (mean+/−s.e.m.).

Figure 4:
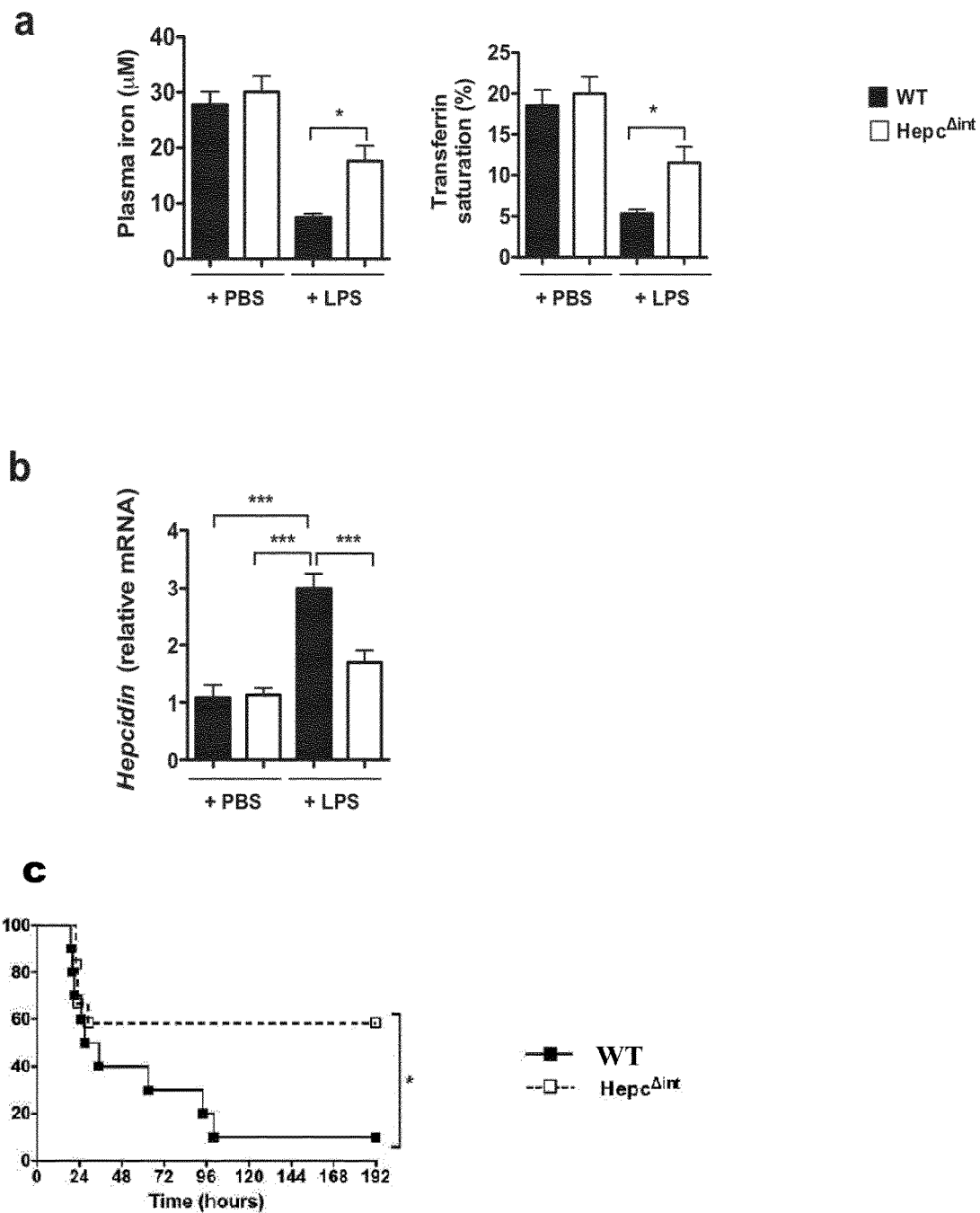

FIG. 4. Iron parameters in WT and Hepc$^{\Delta int}$ mice a, Plasma iron and transferrin saturation in WT (black bars) and Hepc$^{\Delta int}$ (open bars) mice after PBS or LPS injection (n=10) (mean+/−s.e.m.). ns: not significant; $*p<0.05$; $p<0.01$; $*p<0.001$; $**p<0.0001$. b, Expression of hepcidin in liver 7 h after PBS or LPS injection (Q-PCR). (n=10 per group; bars represent mean+/−standard error of the mean (s.e.m.); $*p<0.001$). c, Kaplan-Meier survival curve following i.p. LPS (30 mg/kg) injection in WT (n=10) and Hepc$^{\Delta int}$ (n=12). Statistical analysis by a Log-Rank (Mantel-Cox) test. $*p<0.05$.

Figure 5:
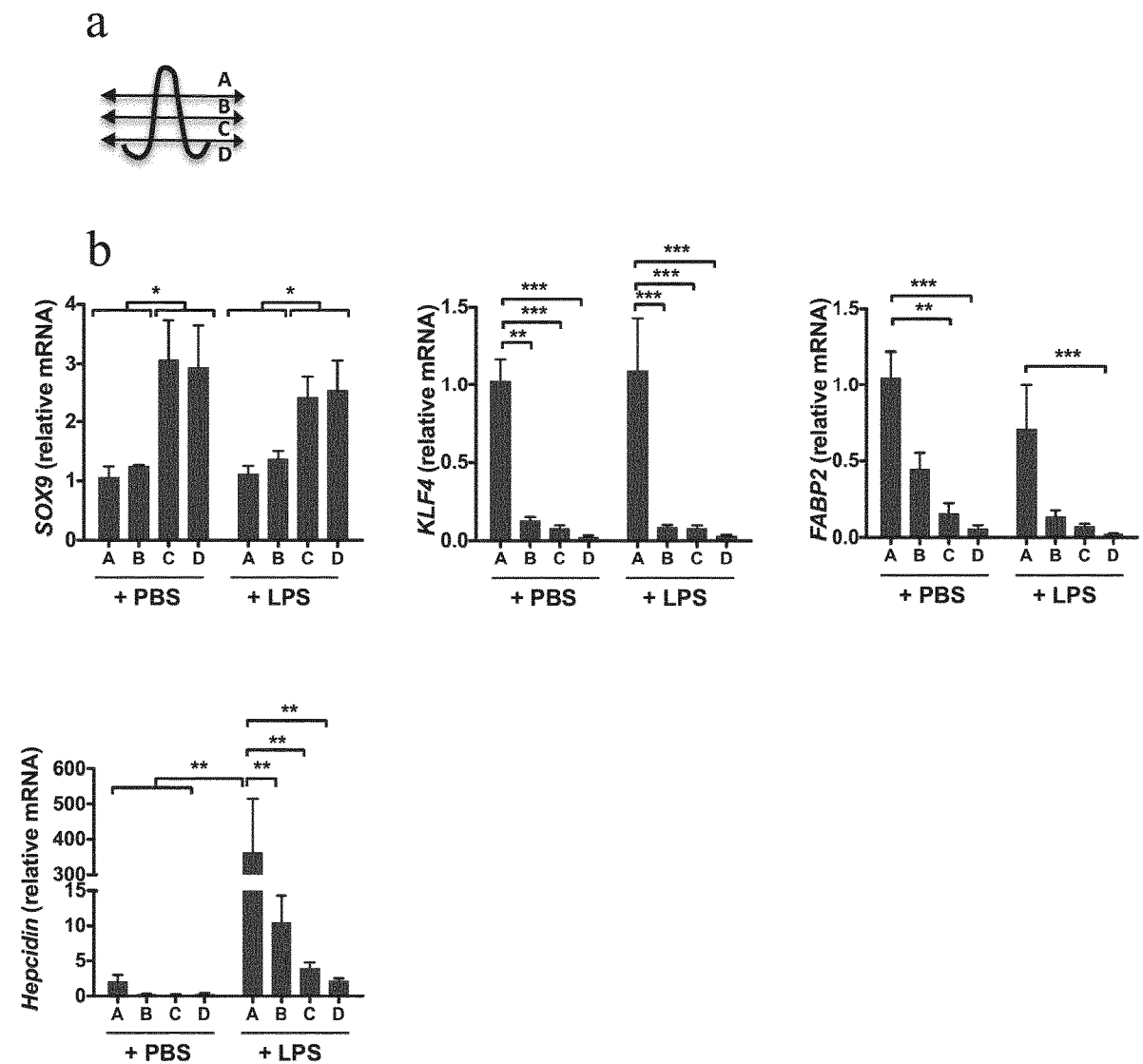

FIG. 5. Hepcidin is expressed in the differentiated compartment of the intestinal epithelium.

a, Scheme of the fractionation of an intestinal villus. b, Tissue fractionation procedure was validated by quantitative PCR analysis of either villus (Fabp2, and KLF4) or crypt intestinal markers (Sox9). Expression of hepcidin in the duodenum 7 h after PBS or LPS injection (Q-PCR). n=4 per group; bars represent mean+/−s.e.m.; $*p<0.05$; $p<0.01$; $*p<0.001$.

Figure 6:
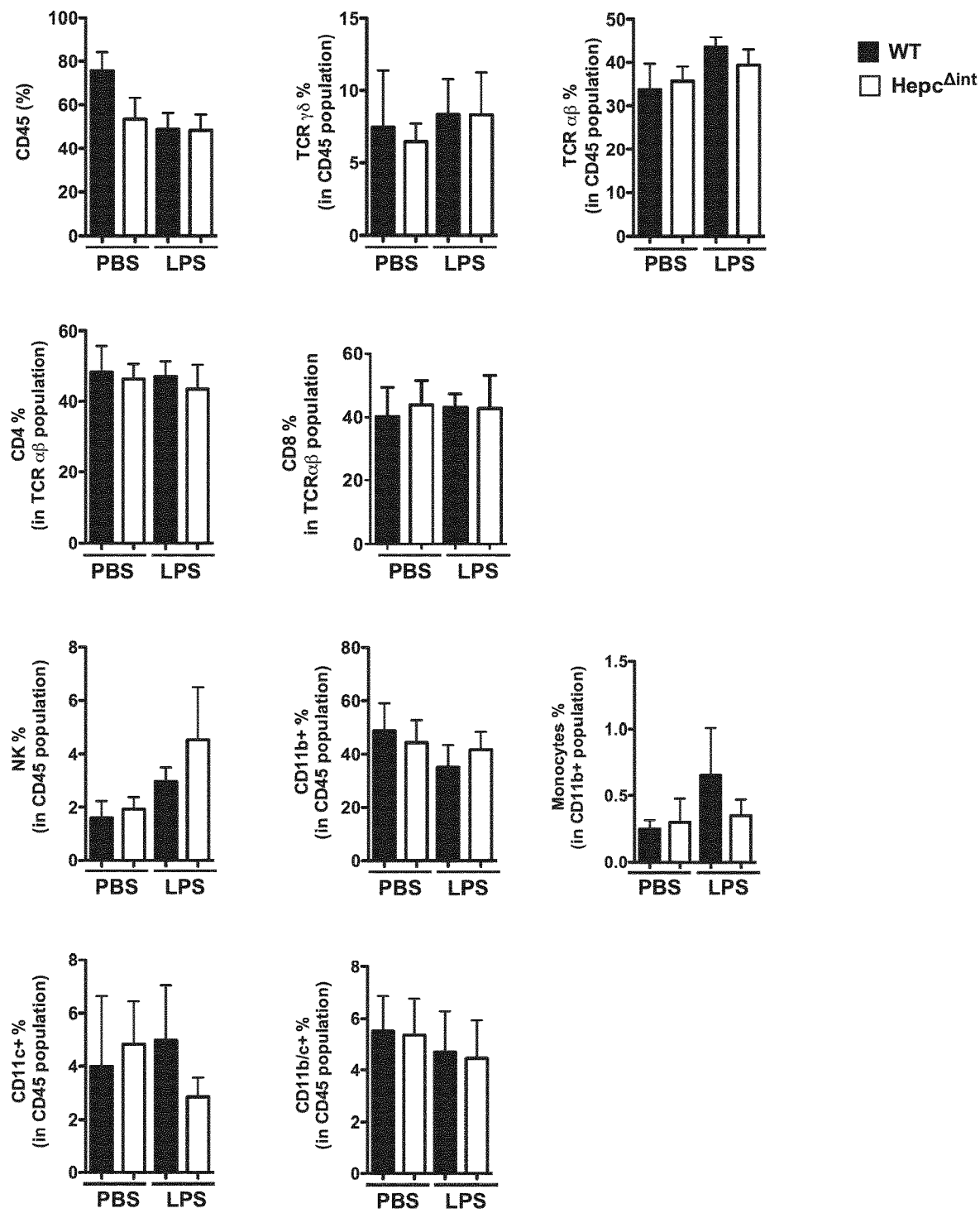

FIG. 6. Immune cell population in lamina propria.

Flow cytometry analysis on lamina propria of the small intestine of WT (black square) and Hepc$\Delta$int (open square) mice 7 h after PBS or LPS injection. n=4 mice per group; Bars represent mean+/−s.e.m.

Figure 7:
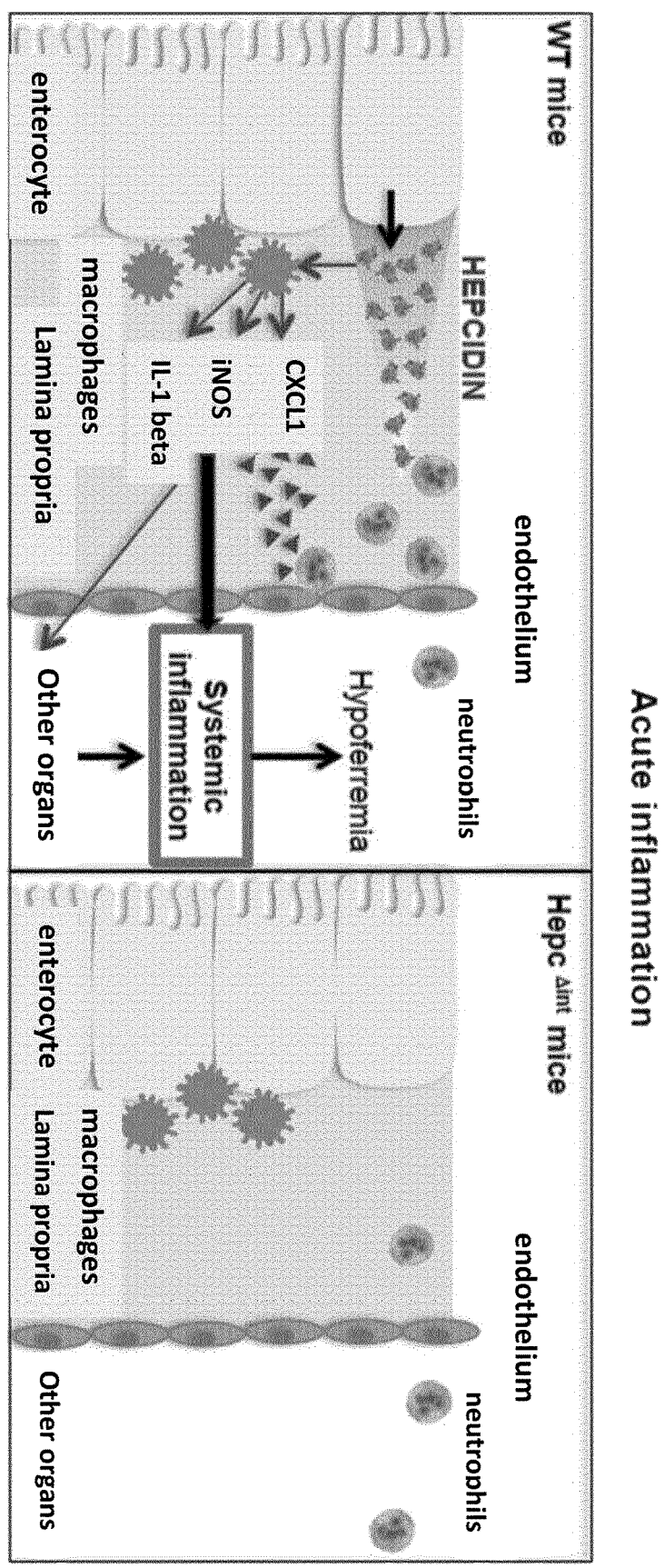

FIG. 7. A proposed model for the mechanisms linking intestinal hepcidin to systemic inflammation.

Figure 8:
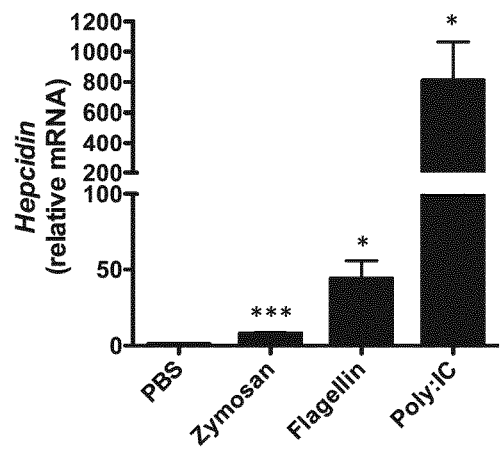

FIG. 8. TLRs agonists induce hepcidin expression in the intestine. Q-PCR on duodenal extracts of WT and Hamp$\Delta$int mice injected for 7 hours with Zymosan, Flagellin, Poly:IC or PBS. n=3 per group; bars represent mean+/−s.e.m.; $*p<0.05$; $***p<0.001$.

Figure 9:
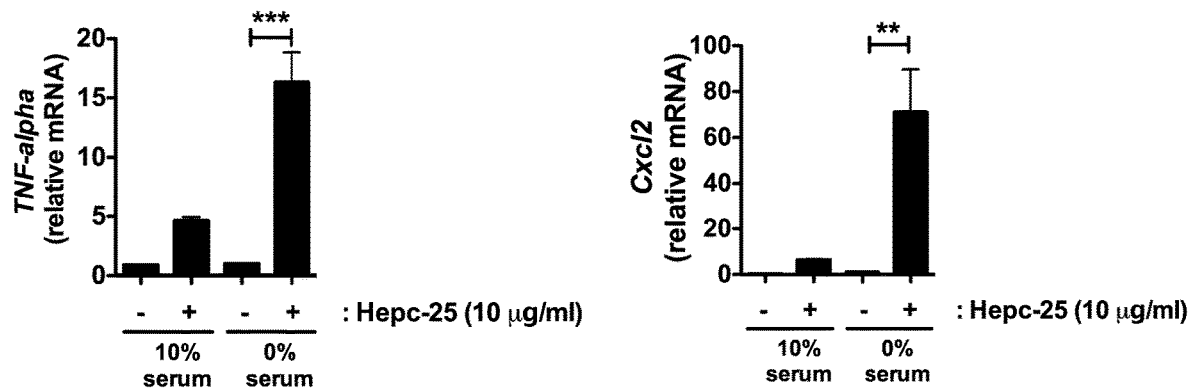

FIG. 9: Serum starvation enhances the proinflammatory action of Hepc-25 in macrophages. Expression by Q-PCR of CXCL2 and TNF-α in Raw 264.7 (ATCC® TIB-71™) murine macrophage cell line serum starved or not for 1 hour before the addition of 10 μg/ml of Hepc-25 (Peptide International) for an additional hour. N=3 per group; mean+/−s.e.m. Statistical analysis by a two-way analysis of variance (ANOVA) followed by a Bonferroni posttest. $p<0.01$; $*p<0.001$.

Figure 10:
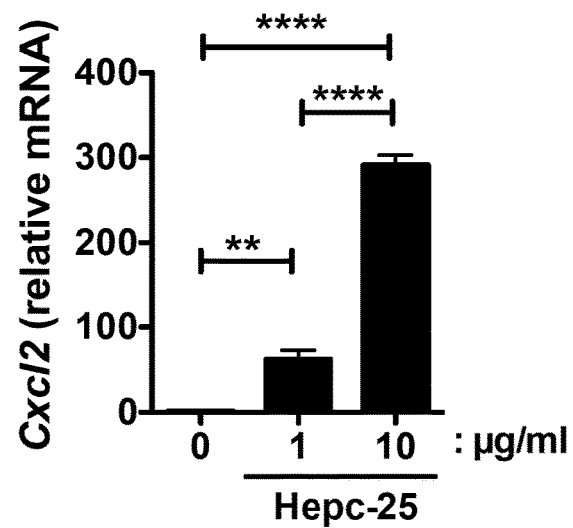

FIG. 10: Hepc-25 induces a robust expression of Cxcl2 at 1 μg/ml in conditions of serum starvation. Expression by Q-PCR of CXCL2 in Raw 264.7 (ATCC® TIB-71™) murine macrophage cell line serum starved for 1 hour or not before the addition of 1 or 10 μg/ml of Hepc-25 (Peptide International) for an additional hour. N=3 per group; mean+/−s.e.m. Statistical analysis by a two-way analysis of variance (ANOVA) followed by a Bonferroni posttest. $p<0.01$; $**p<0.0001$.

Figure 11:
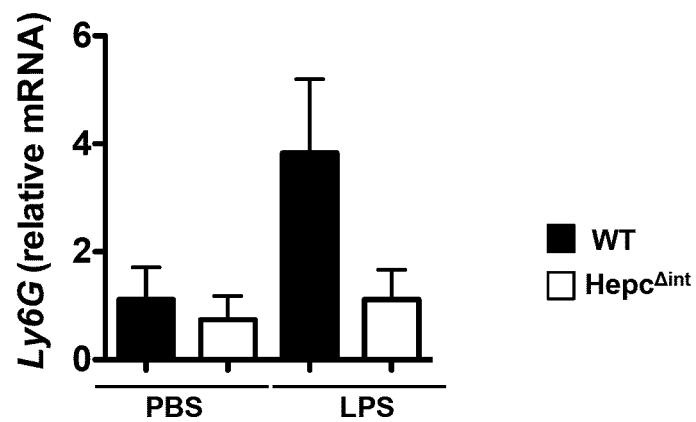

FIG. 11: Intestinal deletion of hepcidin in the intestine prevents neutrophil migration in the intestine. Ly6G expression by Q-PCR in intestine of WT and Hepc$\Delta$int mice after 7 hours PBS or 2 mg/kg LPS injection. n=5 per group; mean+/−s.e.m.

Figure 12:
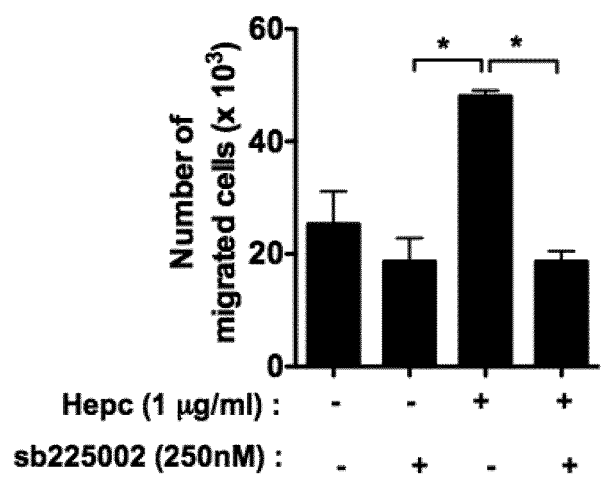

FIG. 12: Inhibition of Cxcr2 prevents neutrophil migration towards hepcidin. Migration of WT bone marrow isolated neutrophils in response to hepcidin (1 μg/ml) in presence or not of the Cxcr2 inhibitor (sb225002, Sigma-Aldrich). n=3. mean+/−s.e.m. It indicates that Cxcr2 may be the receptor of hepcidin in neutrophils

EXAMPLES

Hepcidin is a 25 amino acid peptide demonstrated to be the key iron regulatory hormone, produced by the liver, capable of blocking iron absorption from the duodenum and iron release from macrophages[1]. Here, is disclosed a completely new role of hepcidin in the intestine. The gut is the motor of the systemic inflammatory response in critical illness but the mechanisms by which it acts is unclear[2]. While, during acute inflammation, hepcidin has been shown to be poorly induced in the liver[3,4], it has been found here that it was highly produced by the intestinal epithelium. Our results showed that gut hepcidin acts both as a neutrophil chemoattractant protein and a proinflammatory molecule. Generation of intestinal specific hepcidin KO mice demonstrated that gut hepcidin was required for the recruitment of intestinal neutrophils and the induction of chemokines (CXCL1, CXCL2) and proinflammatory molecules by the macrophages. Importantly, hepcidin is critical to the systemic production of key inflammatory cytokines (IL-6, KC/GRO, TNF, IL-1beta . . . ) and the setting of the hypoferremia of inflammation. Therefore, this study unravels intestinal hepcidin as a critical component to systemic inflammation initiation and a potential new target in systemic inflammatory diseases, which currently lack effective therapeutics.

Figure 1:
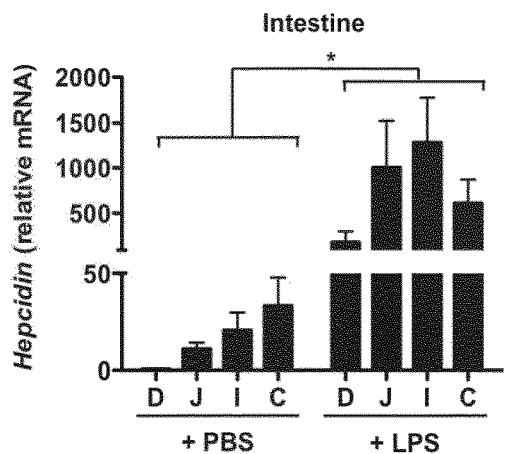
FIG. 1. LPS induced intestinal hepcidin expression a, Expression of hepcidin in intestine (duodenum (D), Jejunum (J), Ileum (I), colon (C)) 7 h after PBS or LPS injection (Q-PCR). (n=4 per group; bars represent mean+/− standard error of the mean (s.e.m.); $*p<0.05$). b, Scheme representing the generation of the Hepc$^{\Delta int}$ mice (top). Hepcidin expression in intestine and liver of WT (black bars) and Hepc$^{\Delta int}$ (open bars) mice (n=5 per group; bars represent mean+/−s.e.m.); $**p<0.01$; $*p<0.05$). c, Hepcidin expression in intestine of WT (black bars) and Hepc$^{\Delta int}$ (open bars) mice after PBS or LPS injection (n=5) (mean+/−s.e.m; $*p<0.05$).
Figure 1:
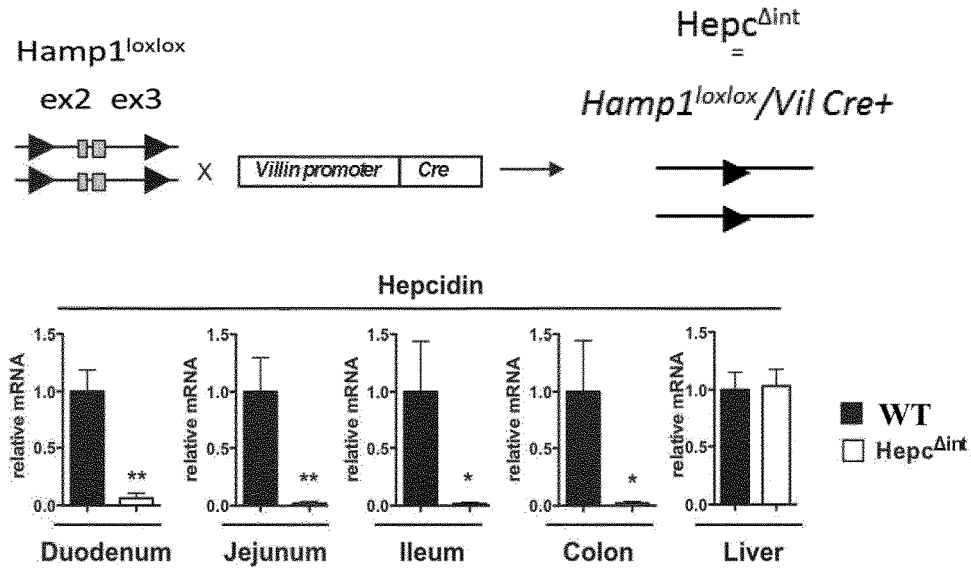
Figure 1:
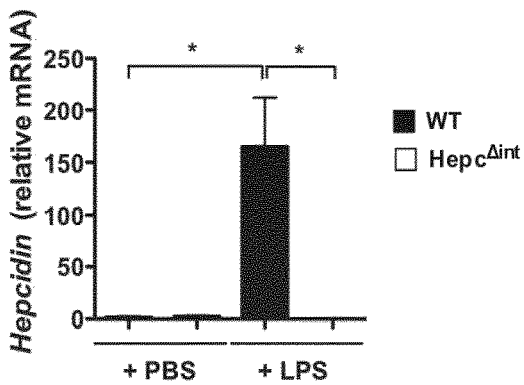

If hepatic hepcidin is now recognized as the key iron regulatory hormone[5], it was originally identified as a cationic antimicrobial peptide (AMP)[6]. However, the potential expression and role of hepcidin in intestinal epithelia, a major source of AMPs, has never been investigated. In this study, basal hepcidin mRNA level was detected in murine intestine, with an increasing expression gradient from the duodenum to the colon of WT mice (FIG. 1a). As the gut is considered as the motor of systemic inflammation[2], a major cause of morbidity and mortality across many diseases, it has herein been investigated whether intestinal hepcidin expression was modified under these conditions. WT Mice were challenged intraperitonealy (ip) with the immune activator lipopolysaccharide (LPS), which derives from the Gram-negative bacterial cell wall. Seven hours after LPS induction, we found a marked increase of hepcidin gene expression in all the segments of the intestine (FIG. 1a) in contrast to the modest induction in the liver, as previously reported[3,4] (FIG. 4b). Using a sequential isolation of intestinal epithelial cells along the crypt villus axis (CVA) (FIG. 5a), we determined that hepcidin expression was restricted to mature differentiated intestinal cells, its expression being undetectable in the proliferative crypt compartment (FIG. 5b). After LPS stimulation, hepcidin was maximally expressed in villus cells with an increasing gradient along the CVA. LPS is a microbial activator of TLR4, a pattern recognition molecule critical for initiating innate immune signaling cascades and proinflammatory responses. TLR4 expression by intestinal epithelial cells is low at basal level, but increases during inflammation (Abreu et al., Nat Rev Immunol 10, 131-144, 2010). The inventors have further demonstrated that the loss of TLR4 clearly reduced the LPS induced-level of hepcidin in the gastrointestinal tract (Data not shown) demonstrating that the hepcidin response to LPS was TLR4-dependent.

To determine the role of gut-derived hepcidin, mice with specific invalidation of hepcidin in the intestinal epithelium (Hepc$^{lox/lox}$-VillinCre: Hepc$^{\Delta int}$) were generated. Those were obtained by breeding recently generated Hamp1$^{lox/lox}$ mice[8] with a transgenic strain expressing the Cre recombinase under the control of the murine villin promoter[9] (FIG. 1b). The deletion efficiency of hepcidin in isolated epithelial cells of the small and large intestines was approximately 97% as determined by quantitative PCR on mouse genomic DNA (data not shown). It confirmed that hepcidin mRNA levels were totally abolished in the intestine (duodenum, jejunum, ileum, colon) of the Hepc$^{\Delta int}$ mice and not affected in the liver of these mice compared to WT mice (FIG. 1b). Hepcidin was not induced in the purified intestinal cells enriched in enterocytes of Hepc$^{\Delta int}$ mice upon LPS injection, confirming that the intestinal epithelial cells are the source of hepcidin production (FIG. 1c).

Figure 2:
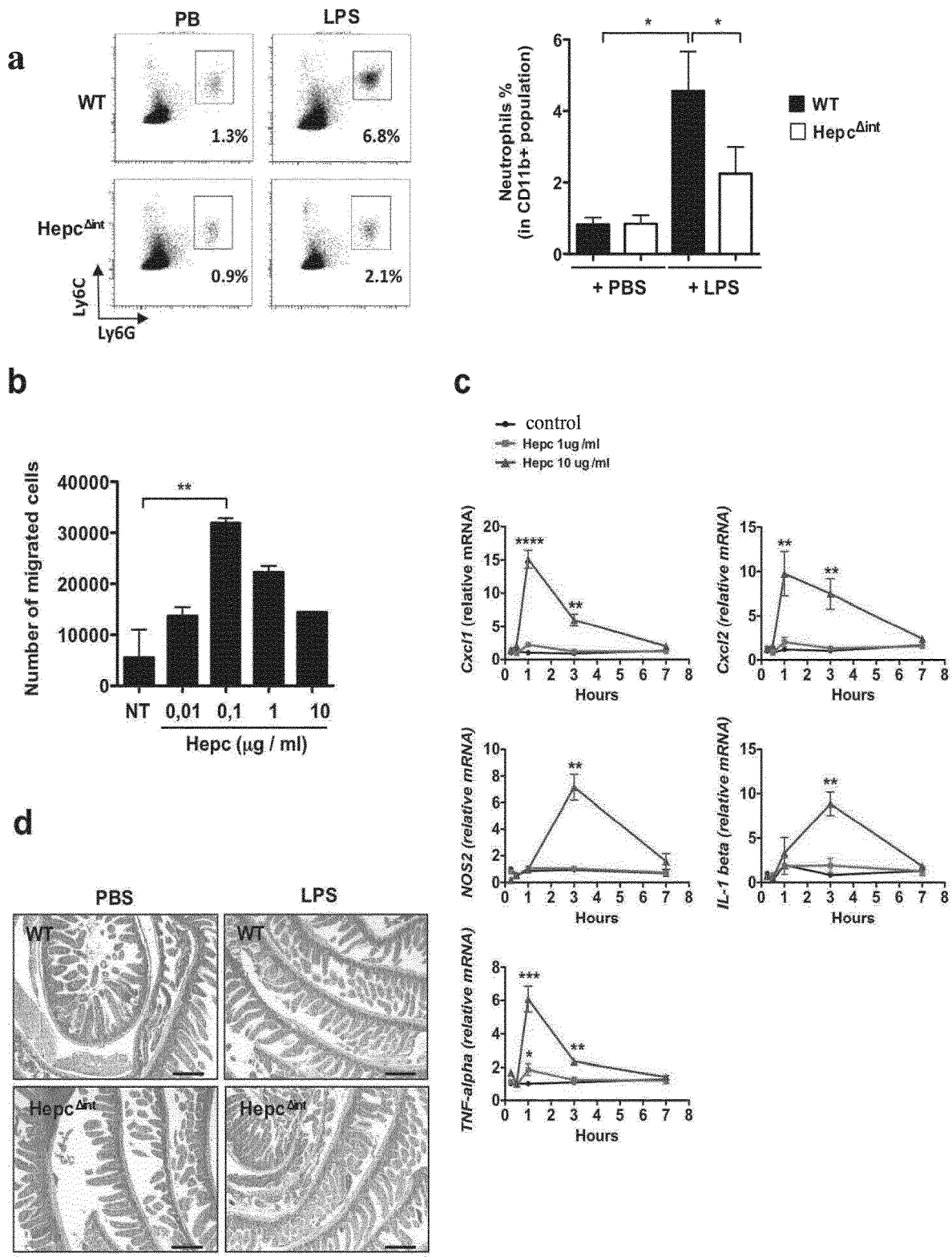
FIG. 2. Hepcidin is a chemoattractant and proinflammatory molecule a, Flow cytometry analysis of neutrophils in lamina propria of WT and KO mice. Left: Representative experiment with Ly6G$^+$ Ly6C$^{low}$ cells shown after gating on CD45$^+$CD11b$^+$ cells; Right: pool of four experiments (mean+/−s.e.m; $*p<0.05$). b, Migration of WT bone marrow isolated neutrophils in response to hepcidin-25. (3 experiments performed in triplicate; mean+/−s.e.m; $*p<0.05$). c, CXCL1, CXCL2, IL-1beta, iNOS mRNA levels in macrophages incubated for 1 or 3 hours with 1 μg/ml, 10 μg/ml Hepcidin-25 or PBS (control). d, Immunohistochemistry using anti-mouse iNOS antibody on intestine of WT and Hepc$^{\Delta int}$ mice upon PBS or LPS injection.

It is now well established that in addition to their barrier and absorptive functions, intestinal epithelial cells can be activated to produce mediators that recruit, activate and condition cells of the immune system[10-12] In particular, during intestinal inflammation, cytokines and chemokines have been reported as critical regulators for recruitment and infiltration of the major effectors of acute inflammation, i.e. the neutrophils, the first leukocytes to be recruited to an inflammatory site[13]. As gut-derived hepcidin expression is induced upon acute systemic inflammation, flow cytometric analyses were performed to determine whether locally it could contribute to the recruitment of immune cells in the lamina propria. Among all the tested immune populations (FIG. 6), only neutrophils were recruited upon LPS injection (FIG. 2a). Importantly, the deletion of intestinal hepcidin decreased neutrophil population by almost two fold (FIG. 2a) suggesting that intestinal hepcidin contributed to the recruitment of neutrophils in the intestine after LPS injection.

Following LPS stimulation, the intestine of WT mice was severely inflamed as demonstrated by a high expression level of inducible nitric oxide synthase (NOS2), an essential provider for NO-mediated signaling during the initiation of systemic inflammation[22] (Data not shown). In sharp contrast, the Hepc$^{\Delta int}$ mice intestine had a dramatic reduction of NOS2. Addition of synthetic mature hepcidin on the basolateral or apical side of the Caco-2 intestinal cell line did not induce iNOS expression (data not shown) nor increased the expression of inflammatory cytokines, such as TNF-α or the neutrophil chemokine IL-8.

Hepcidin was originally identified as a cationic AMP by its close structural similarity to the beta defensins[6]. Hepcidin contains disulfide bridges, highly conserved among vertebrates, like typical chemokine proteins (C, CC, CXC, CX$_3$C), which contain intramolecular disulfide bonds critical for their functions. Through a close analysis of 1-D sequences and 3-D structural alignments of hepcidin with chemokines, the inventors highlighted the striking structural similarity of hepcidin with known chemokines (CCL5, CCL11, CCL20, and XCL1; Data not shown), and therefore hypothesized that hepcidin could display a direct chemokine function. They thus tested the ability of synthetic hepcidin to attract purified neutrophils using a classical migration assay. As shown in FIG. 2b, hepcidin induced a dose-dependent migration of neutrophils in the typical bimodal manner[14-16] demonstrating for the first time that hepcidin displays chemoattractant properties. The peak response was observed at 0.1 µg/ml, a dose at which prototypical AMPs exert maximum chemotaxis[14-16]. As disclosed in FIG. 11, intestinal deletion of hepcidin in the intestine prevents neutrophil migration in the intestine.

By studying the direct chemoattractant effect the inventors have observed that inhibition of Cxcr2 was also able to prevent neutrophil migration (see FIG. 12). These results clearly suggest that Cxcr2 may be the receptor of hepcidin in neutrophils.

The gastrointestinal tract contains the largest reservoir of macrophages in the organism[17]. Besides its proper chemoattractant property, the inventors hypothesized that hepcidin may influence the production of chemokines by the macrophages. Macrophages were incubated with hepcidin-25 at different time points (30 min, 1 h, 3 h, 24 h, 48 h). At 1 hour, the expression of the specific neutrophil chemoattractants CXCL-1 and CXCL2, was slightly increased with 1 µg/ml hepcidin and maximally induced with 10 µg/ml hepcidin, suggesting that hepcidin may also indirectly promote neutrophil migration through macrophage-induced specific neutrophil chemoattractants such as CXCL-1 and CXCL2, thus contributing to neutrophil recruitment cascade (FIG. 2c). Strikingly, the only set of genes statistically induced by hepcidin at 1 hour (with a fold change >2) was involved in the inflammatory response: TNF-α, the neutrophil-specific chemoattractants CXCL1 and CXCL2, NF-kappa-B inhibitor zeta, an atypical IκB family member and transcriptional coactivator required for the selective expression of a subset of NF-κB target genes (Hildebrand et al., J Immunol 190, 4812-4820, 2013) and Mir-146, recently demonstrated to have a critical role in limiting an excessive acute inflammatory reaction (Brudecki et al., Immunol Cell Biol 91, 532-540, 2013) (Data not shown).

Kinetic response of macrophage-derived CXCL1 and TNF-α following hepcidin treatment was further determined. Transient mRNA induction peaked at 1 hour, suggesting a direct proinflammatory effect of hepcidin. Massive protein accumulation of CXCL1 and TNF-α reached respectively 300 and 150 pg/ml at 7 hours (Data not shown).

Hepcidin stimulated IL-1beta, IL-6 and iNOS expression with a maximal induction at 3 hours with 10 µg/ml hepcidin (FIG. 2c) while the peak of TNF-alpha and Cox-2 expression occurred after 1 hour of hepcidin treatment. AMPs, such as LL37, typically function in this high concentration range[18,19] to induce proinflammatory molecules[20,21]. This allows the production of inflammatory mediators in pathological conditions where AMPs concentrations can reach high values[18,19] and not in healthy tissues where inflammatory damage might otherwise harm host cells. Altogether, these data reveal for the first time that hepcidin functions as both a chemoattractant for neutrophils and a regulator of immune response through induction of proinflammatory mediators by macrophages. Importantly, this new proinflammatory role of hepcidin was independent of its known role in iron homeostasis as the expression of the iron-responsive gene TfR1, was unchanged by the addition of hepcidin (Data not shown) and supplementation of iron or iron chelators did not modify either the expression of inflammatory genes (data not shown).

The inventors have further demonstrated that inhibition of the MAPK, PI3K and AKT pathways had no effect on the hepcidin-induced expression of CXCL1 and TNF-α. In contrast, inhibitors of the NF-kB pathway (BAY 7082 and BAY 7085) strongly blunted the hepcidin-induced expression of these genes (Data not shown). Moreover, MyD88, a canonical adaptor for inflammatory signaling pathway, but not TLR4, was required for the hepcidin-triggered induction of CXCL1 and TNF-α. Indeed, macrophages isolated from TLR4−/− but not MyD88−/− mice were still able to mount an inflammatory response after addition of hepcidin.

As disclosed in FIGS. 9 and 10, the stimulatory effect of hepcidin on macrophage-mediated cytokine release in clearly enhanced in serum-free conditions.

Upon LPS stimulation, the intestine of the WT mice was largely inflamed with a high expression of iNOS (FIG. 2d), iNOS-derived NO acting as a signalling element essential for the initiation of systemic inflammation[22]. In sharp contrast to this LPS-induced inflammation of the WT mice intestinal mucosa, we observed a dramatic reduction of the inflammatory status of the Hepc$^{\Delta int}$ mice intestine with almost no immunostaining of iNOS.

Figure 3:
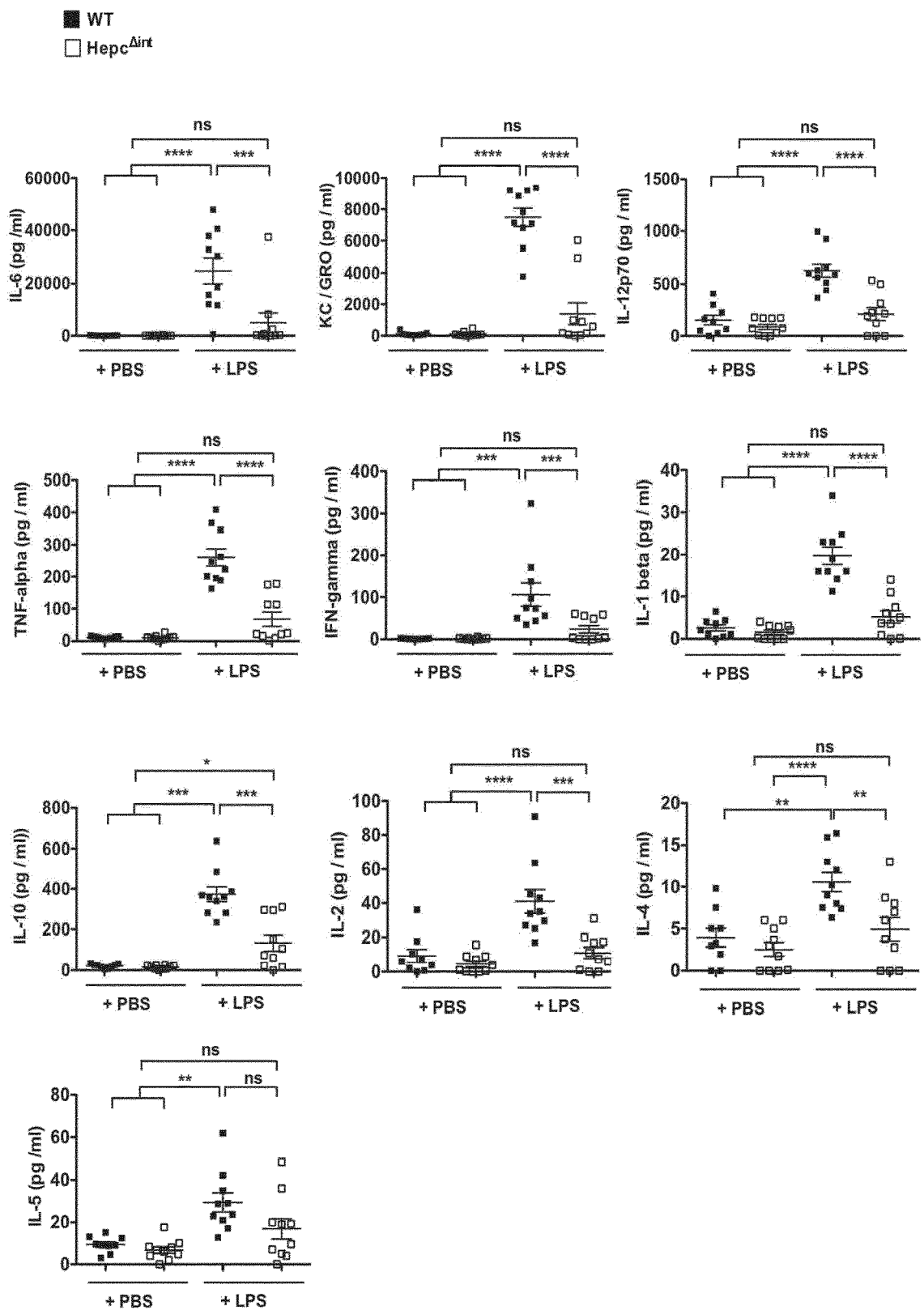
FIG. 3. Intestinal hepcidin is required for systematic inflammation

The effect of intestinal hepcidin deletion on systemic inflammation has been further evaluated by measuring blood cytokinic expression profile in WT and mutant mice. As expected, acute inflammation induced by ip LPS injection highly increased the production of proinflammatory cytokines in the plasma of WT mice, with the highest expression of IL-6 and CXCL-1 (KC/GRO). Strikingly, deletion of intestinal hepcidin largely blunted the production of IL-6, CXCL-1 (KC/GRO), IL-12p70, TNF, IFN-gamma, IL-1beta, IL-2, IL-5 and IL-4 (FIG. 3) and also largely prevented the production of the anti-inflammatory cytokine, IL-10. This dramatic result shows that intestinal hepcidin is critically required for triggering systemic inflammation upon LPS stimulation, its deficiency mimicking the phenotype of mice made deficient for the LPS receptor, TLR4[23].

Under physiological conditions, hepatic hepcidin is the predominant reservoir for systemic hepcidin[8] and controls serum iron levels by regulating intestinal iron absorption and macrophage iron recycling. Hepatic hepcidin is induced by many inflammatory cytokines, such as IL-6[25], TLR-agonists and pathogens[26] and has therefore been proposed to be responsible for the hypoferremia of inflammation[27]. To determine to what extent the high production of hepcidin produced by the intestine after acute inflammation could contribute to the hypoferremia of inflammation, iron levels in both WT and mutant mice were measured. At basal level, Hepc$^{\Delta int}$ mice presented similar iron levels than WT littermates. However, upon inflammation, the decrease in plasma iron and transferrin saturation observed in WT mice was blunted in the Hepc$^{\Delta int}$ mice (FIG. 4a), suggesting that intestinal hepcidin is participating to the mechanisms leading to hypoferremia. The increase in hepatic hepcidin in WT mice prevented in the mutant mice was correlated to the level of inflammation (FIG. 4b). It has been proposed that hepcidin evolved from an antimicrobial peptide to an iron-regulatory hormone. However, the data presented herein suggest that hypoferremia of inflammation is triggered by the evolutionary conserved pleiotropic effects of hepcidin, as an AMP.

Inflammatory cytokines, released in massive amounts in response to bacterial toxins such as LPS, are important biological mediators of sepsis, a major cause of mortality and morbidity. Importantly, we found that whereas challenge of WT mice with lethal doses of LPS provoked only 10% survival by 96 h, Hepc$^{\Delta int}$ mice experienced 58% survival (FIG. 4c).

Although the results presented here were performed with classical TLR4 agonist LPS, hepcidin expression in the intestinal epithelium was likewise induced by zymosan, flagellin, and poly:IC, agonists of TLR2, TLR5, and TLR3 respectively, suggesting that hepcidin may be a convergence point in inflammatory response to a wide array of microbial triggers (FIG. 8).

Clinical relevance of the inflammatory role of hepcidin in intestine was further assessed using the DSS-induced colitis model, mimicking some characteristics of human inflammatory bowel diseases. The expression of NOS2, IL-17A and TNF-α, key proinflammatory cytokines in the setting of human IBDs (Duma et al., 2011; Leppkes et al., Gastroenterology 136, 257-267, 2009; Neurath et al., Eur J Immunol 27, 1743-1750 1997), are stronly induced in the colon of DSS-induced WT mice, but was significantly dampened in Hepc$^{\Delta int}$ littermates compared to WT mice (FIG. 5C). Intestinal hepcidin may therefore have a protective role in IBDs by regulating cytokines, important for epithelial repair.

Finally, the inventors have analyzed the hepcidin expression in the colonic mucosa of healthy subjects CD patients and UC patients. In healthy subjects, hepcidin immunoreactivity was concentrated apically in colonic epithelial cells. Its expression was increased and relocated to the basolateral surface and into the cytoplasm of the intestinal epithelium as well as in the lamina propria in CD and UC patients.

Herein is disclosed a new model where hepcidin acts as an intestinal chemokine to trigger neutrophil infiltration and macrophage activation in the lamina propria and provoking a systemic inflammatory response (FIG. 7).

The systemic inflammatory response is biologically complex and had led to the failure of hundreds clinical trial strategies to modify the systemic inflammatory response by targeting endogenous mediator molecules[28]. The gut is considered for many years as a cytokine-generating organ in systemic inflammation[29]. However, there is currently no unifying hypothesis that encompasses the diverse ways in which the gut influences outcome in critical illness[30]. Importantly, the results presented herein bring a new paradigm and show that the trigger of systemic inflammation depends on the induction of a single gut-derived molecule: hepcidin. It therefore opens new therapeutics avenues in the treatment of inflammatory diseases.

Methods

Mice

Hamp1$^{lox/lox}$ mice[8] were bred with villin-Cre transgenic mice[9], in which the Cre recombinase is under the control of the murine villin promoter. Studies were performed in a mixed C57BL6/129SV genetic background, using male littermates.

The animal studies described here were reviewed and approved (Agreement no CEEA34.CP.003.13) by the "Président du Comité d'Ethique pour l'Expérimentation Animale Paris Descartes" and are in accordance with the principles and guidelines established by the European Convention for the Protection of Laboratory Animals (Council of Europe, ETS 123, 1991).

Mice were ip injected with LPS (from *E. coli* O111:B4; 2 mg/kg), Zymosan A (from *Saccharomyces cerevisiae*, Sigma-Aldrich Z4250; 250 mg/kg), Poly:IC (Polyinosinic-polycytidylic acid sodium salt, Sigma-Aldrich P0913; 12.5 mg/kg), Flagellin (FLA-ST from *Salmonella Typhimirium*, InvivoGen, #12B06-MM; 1.5 mg/kg) or with a sterile saline solution (PBS) and sacrificed 7 hours later.

Fractionation of Murine Epithelial Cells

The sequential isolation of mouse small intestinal epithelial cells along the crypt villus axis has been previously described and validated[31-33].

Briefly, mice were sacrificed by cervical dislocation. The duodenum was removed separately, tied off at one end, everted and filled to distension with phosphate buffered saline (PBS) prior to closing the remaining open end. It was then incubated with shaking at 37° C. for 10 min in 20 ml of citrate buffer (96 mMNaCl, 1.5 mMKCl, 27 mMNa-citrate, 8 mM KH2PO4, 5.6 mM Na2HPO4, and 1 mM dithiothreitol (DTT), pH 7.3). Duodenum was then transferred in an EDTA buffer (PBS containing 1.5 mM EDTA, and 0.5 mM DTT) to a 37° C. shaking incubator and dissociated epithelial cells were collected after each of 4 consecutive incubation steps lasting 10 min (fraction A), 10 min (fraction B), 30 min (fraction C), and 20 min (fraction D). Cells isolated in the resulting fractions were harvested by centrifugation at 1500 rpm at 4° C. for 5 min, snap frozen in liquid nitrogen, and stored at −80° C.

Lamina Propria Cell Isolation

Seven hours after PBS or LPS (2 µg/g) injection, mice were sacrificed and the small and large intestine were harvested. After Peyer's patches removal, the tissue was opened longitudinally and washed in $Ca^{2+}/Mg^{2+}$-free PBS containing 100 U/ml Penicillin, 100 µg/ml Streptomycin (GIBCO), 100 U/ml polymixin B (Sigma-Aldrich). Next, the tissue was cut into 1 cm pieces and incubated twice in $Ca^{2+}/Mg^{2+}$-PBS containing 2 mM EDTA, 2% FCS, and antibiotics for 20 min at 37° C., vigorously shaking. Tissues were washed for 10 min in $Ca^{2+}/Mg^{2+}$-PBS containing 0.01 M HEPES (GIBCO) and antibiotics, and then minced and incubated in RPMI 1640 containing 0.05 mg/ml Collagenase D (Roche), 0.05 mg/ml DNAse (Roche), and 0.025 mg/ml Hyaluronidase (Roche) for 20 min at 37° C., vigorously shaking. Tissues were then filtered through a 70 µm cell strainer, cells were counted and resuspended in cold $Ca^{2+}/Mg^{2+}$-PBS containing 2% FCS.

Flow Cytometry

The lamina propria cell suspension ($4 \times 10^6$ cells/well) was washed in $Ca^{2+}/Mg^{2+}$-PBS and incubated with LiveDead reagent (Blue fluorescent reactive dye, Invitrogen) for 20 min at room temperature. Prior to staining, Fc receptors were blocked with FcBlock™ (anti-CD16 and anti-CD32, 5 µg/ml, BD Pharmingen) and cells were further incubated 15 min at 4° C. with antibodies in 96-wells round bottom plates with agitation. Cells were either stained with biotinylated anti-Ly6C (myeloid analysis) or biotinylated anti-TCRβ (lymphoid analysis). After 2 washes in PBS 2% FCS, cells were stained with antibodies specific for CD45.2/CD45.1-PerCP-Cy5.5, CD11b-APC, CD11c-PE-Cy7, NK1.1-PE, streptavidin-Pac Blue and Ly6G-FITC (for myeloid analysis) or with antibodies anti-CD45.2-APC, CD4-Pacific Blue, CD8-APC-H7, streptavidin-PE-Cy7, CD19-FITC, NK1-PerCP-Cy5.5 and anti-TCRβ-PE (for lymphoid analysis). All antibodies were purchased from BD Pharmingen, except for the CD11b-APC from eBiosciences. Cells were washed, fixed in 1% paraformaldehyde and stored at 4° C. until further analysis. Cells were acquired using the multicolour flow cytometer Fortessa (BD) and analysed with FACS-DIVA (BD).

Reverse Transcription and Real-Time Quantitative PCR

RNA extraction, reverse transcription, quantitative PCR and sequences of the primers used have been previously described[8]. All samples were normalized to the threshold cycle value for cyclophilin-A.

Cytoplex Assay

Cytokines in the plasma of mice were measured with the V-PLEX Proinflammatory Panel1 (mouse) Kit (Meso Scale Discovery), according to the manufacturer's instruction.

Macrophages

Primary Mouse Bone Marrow-Derived Neutrophils

Bone marrows from WT mice were flushed from femurs and tibias with PBS using a 25 G needle. Tissues were homogenized through a 18 G needle and the suspension was passed through 70 µm and 40 µm cell strainers. Cells were centrifuged at 400 g for 10 min and resuspended in cold MACS buffer (PBS, BSA 0.5%, EDTA 2 mM, pH 7.4). After counting, cells were incubated on ice with FcBlock™ for 10 min, anti-Ly6C for 15 min and anti-biotin antibody microbeads for 15 min, following the manufacturer's instructions. Cells were washed with MACS buffer and centrifuged at 400 g for 10 min. Neutrophils were immuno-magnetically separated following filtration of the cell suspension through an LS column (Miltenyi) according to manufacturer's instructions.

Migration Assay

Neutrophil migration was assessed using transwell (3 µm; BD-Falcon) coated with 10 µg/ml fibronectin (# F1141, Sigma-Aldrich). The cells ($5 \times 10^5$/well) were diluted in 700 µL DMEM+10% SVF and migration towards hepcidin (Peptide International) in the bottom well was allowed for 2 hours at 37° C. The resulting migrated cells recovered from the bottom well were counted using hemocytometer.

Immunostaining

Tissues were fixed in 4% formaldehyde and embedded in paraffin. Sections were subjected to antigen retrieval in a pressure cooker for 15 min at 95° C., blocking endogenous peroxidases and immunohistochemistry with mouse anti-iNOS primary antibody (BD Biosciences ref. 610328) 1 h30 at room temperature. Bound primary antibody was detected by sequential incubation of the samples with goat anti-mouse biotinylated IgG's (Vector BA-9200) and streptavidin/horseradish peroxidase (VECTOR, Vectastain ABC Kit, PK-6100) for 30 min at room temperature. iNOS was revealed with DAB method (VECTOR, ImmPACT Nova-RED SK4805). Images were captured with a light microscope using a 10× resolution objective (Leica DMI 3000 B).

Iron Measurements

Plasma iron was quantified colorimetrically by a previously described method[34].

1-D Sequence Alignment Method

Clustal W/X version 2.0[35] has been used to carry out the 1-D sequence alignment. Clustal programs incorporate a position-specific scoring scheme and a weighting scheme for down weighting over-represented sequence groups. All pairs of sequences to be aligned are compared by pair-wise alignment and a score matrix of similarity has been produced, indicating the divergence or similarities of each pair. The "quality score" represents the main method of alignment and has been performed with default parameters[36].

3-D Structural Alignment Method

TM-align algorithm[37] has been used to perform 3-D structural alignment between protein pairs. This method combines the TM-score rotation matrix[38] and dynamic programming[39]. TM-align only employs the backbone C-alpha coordinates of the given protein structures. TM-align process combines two methods that are initial alignments and heuristic iterative algorithm. Initial alignments are exploited using dynamic programming and then heuristic iteration using TM-score rotation.

Statistical Analysis

Analysis was performed using GraphPad Prism 5.0 and the significance of experimental differences was evaluated by a t-test or one-way ANOVA analysis followed by a Bonferroni posttest.

REFERENCES

Throughout this application, various references describe the state of the art to which this invention pertains. The disclosures of these references are hereby incorporated by reference into the present disclosure.

1 Nicolas, G. et al. Lack of hepcidin gene expression and severe tissue iron overload in upstream stimulatory factor 2 (USF2) knockout mice. *Proc. Natl. Acad. Sci. U.S.A.* 98, 8780-8785 (2001).
2 Mittal, R. & Coopersmith, C. M. Redefining the gut as the motor of critical illness. *Trends Mol Med* 20, 214-223, doi:10.1016/j.molmed.2013.08.004 (2014).
3 Lou, D. Q. et al. Iron- and inflammation-induced hepcidin gene expression in mice is not mediated by Kupffer cells in vivo. *Hepatology* 41, 1056-1064, doi:10.1002/hep.20663 (2005).
4 Roy, C. N. et al. An Hfe-dependent pathway mediates hyposideremia in response to lipopolysaccharide-induced inflammation in mice. *Nat Genet* 36, 481-485, doi:10.1038/ng1350 (2004).
5 Ganz, T. Systemic iron homeostasis. *Physiol Rev* 93, 1721-1741, doi:10.1152/physrev.00008.2013 (2013).
6 Krause, A. et al. LEAP-1, a novel highly disulfide-bonded human peptide, exhibits antimicrobial activity. *FEBS Lett.* 480, 147-150 (2000).
7 Bastide, P. et al. Sox9 regulates cell proliferation and is required for Paneth cell differentiation in the intestinal epithelium. *J Cell Biol* 178, 635-648, doi:10.1083/jcb.200704152 (2007).
8 Zumerle, S. et al. Targeted disruption of hepcidin in the liver recapitulates the hemochromatotic phenotype. *Blood* 123, 3646-3650, doi:10.1182/blood-2014-01-550467 (2014).
9 el Marjou, F. et al. Tissue-specific and inducible Cre-mediated recombination in the gut epithelium. *Genesis* 39, 186-193 (2004).
10 Maldonado-Contreras, A. L. & McCormick, B. A. Intestinal epithelial cells and their role in innate mucosal immunity. *Cell Tissue Res* 343, 5-12, doi:10.1007/s00441-010-1082-5 (2011).
11 Rescigno, M. The intestinal epithelial barrier in the control of homeostasis and immunity. *Trends Immunol* 32, 256-264, doi:10.1016/j.it.2011.04.003 (2011).
12 Zaph, C. et al. Epithelial-cell-intrinsic IKK-beta expression regulates intestinal immune homeostasis. *Nature* 446, 552-556, doi:10.1038/nature05590 (2007).
13 Fournier, B. M. & Parkos, C. A. The role of neutrophils during intestinal inflammation. *Mucosal Immunol* 5, 354-366, doi:10.1038/mi.2012.24 (2012).
14 Grigat, J., Soruri, A., Forssmann, U., Riggert, J. & Zwirner, J. Chemoattraction of macrophages, T lymphocytes, and mast cells is evolutionarily conserved within the human alpha-defensin family. *J Immunol* 179, 3958-3965 (2007).
15 Rohrl, J., Yang, D., Oppenheim, J. J. & Hehlgans, T. Human beta-defensin 2 and 3 and their mouse orthologs induce chemotaxis through interaction with CCR2. *J Immunol* 184, 6688-6694, doi:10.4049/jimmunol.0903984 (2010).
16 De, Y. et al. LL-37, the neutrophil granule- and epithelial cell-derived cathelicidin, utilizes formyl peptide receptor-like 1 (FPRL1) as a receptor to chemoattract human peripheral blood neutrophils, monocytes, and T cells. *J Exp Med* 192, 1069-1074 (2000).
17 Smith, P. D. et al. Intestinal macrophages and response to microbial encroachment. *Mucosal Immunol* 4, 31-42, doi:10.1038/mi.2010.66 (2011).
18 Ong, P. Y. et al. Endogenous antimicrobial peptides and skin infections in atopic dermatitis. *N Engl J Med* 347, 1151-1160, doi:10.1056/NEJMoa021481 (2002).
19 Soehnlein, O. et al. Neutrophil secretion products pave the way for inflammatory monocytes. *Blood* 112, 1461-1471, doi:10.1182/blood-2008-02-139634 (2008).
20 van der Does, A. M. et al. LL-37 directs macrophage differentiation toward macrophages with a proinflammatory signature. *J Immunol* 185, 1442-1449, doi:10.4049/jimmunol.1000376 (2010).
21 Yu, J. et al. Host defense peptide LL-37, in synergy with inflammatory mediator IL-1beta, augments immune responses by multiple pathways. *J Immunol* 179, 7684-7691 (2007).
22 Duma, D. et al. NOS-1-derived NO is an essential triggering signal for the development of systemic inflammatory responses. *Eur J Pharmacol* 668, 285-292, doi: 10.1016/j.ejphar.2011.05.065 (2011).
23 Juskewitch, J. E. et al. LPS-induced murine systemic inflammation is driven by parenchymal cell activation and exclusively predicted by early MCP-1 plasma levels. *Am J Pathol* 180, 32-40, doi:10.1016/j.ajpath.2011.10.001 (2012).
24 Kawai, T., Adachi, O., Ogawa, T., Takeda, K. & Akira, S. Unresponsiveness of MyD88-deficient mice to endotoxin. *Immunity* 11, 115-122 (1999).
25 Nemeth, E. et al. IL-6 mediates hypoferremia of inflammation by inducing the synthesis of the iron regulatory hormone hepcidin. *J Clin Invest* 113, 1271-1276, doi: 10.1172/JCI20945 (2004).
26 Armitage, A. E. et al. Hepcidin regulation by innate immune and infectious stimuli. *Blood* 118, 4129-4139, doi:10.1182/blood-2011-04-351957 (2011).
27 Ganz, T. & Nemeth, E. Iron sequestration and anemia of inflammation. *Semin Hematol* 46, 387-393, doi:10.1053/j.seminhematol.2009.06.001 (2009).
28 Marshall, J. C. Why have clinical trials in sepsis failed? *Trends Mol Med* 20, 195-203, doi:10.1016/j.molmed.2014.01.007 (2014).

29 Mainous, M. R., Ertel, W., Chaudry, I. H. & Deitch, E. A. The gut: a cytokine-generating organ in systemic inflammation? *Shock* 4, 193-199 (1995).

30 Clark, J. A. & Coopersmith, C. M. Intestinal crosstalk: a new paradigm for understanding the gut as the "motor" of critical illness. *Shock* 28, 384-393, doi:10.1097/shk.0b013e31805569df (2007).

31 Flandez, M., Guilmeau, S., Blache, P. & Augenlicht, L. H. KLF4 regulation in intestinal epithelial cell maturation. *Exp Cell Res* 314, 3712-3723, doi:10.1016/j.yexcr.2008.10.004 (2008).

32 Mariadason, J. M. et al. Gene expression profiling of intestinal epithelial cell maturation along the crypt-villus axis. *Gastroenterology* 128, 1081-1088 (2005).

33 Smartt, H. J. et al. p27kip1 Regulates cdk2 activity in the proliferating zone of the mouse intestinal epithelium: potential role in neoplasia. *Gastroenterology* 133, 232-243, doi:10.1053/j.gastro.2007.04.043 (2007).

34 Mastrogiannaki, M. et al. HIF-2alpha, but not HIF-1alpha, promotes iron absorption in mice. *J Clin Invest* 119, 1159-1166 (2009).

35 Larkin, M. A. et al. Clustal W and Clustal X version 2.0. *Bioinformatics* 23, 2947-2948, doi:10.1093/bioinformatics/btm404 (2007).

36 Thompson, J. D., Gibson, T. J., Plewniak, F., Jeanmougin, F. & Higgins, D. G. The CLUSTAL_X windows interface: flexible strategies for multiple sequence alignment aided by quality analysis tools. *Nucleic Acids Res* 25, 4876-4882 (1997).

37 Zhang, Y. & Skolnick, J. TM-align: a protein structure alignment algorithm based on the TM-score. *Nucleic Acids Res* 33, 2302-2309, doi:10.1093/nar/gki524 (2005).

38 Zhang, Y. & Skolnick, J. Scoring function for automated assessment of protein structure template quality. *Proteins* 57, 702-710, doi:10.1002/prot.20264 (2004).

39 Needleman, S. B. & Wunsch, C. D. A general method applicable to the search for similarities in the amino acid sequence of two proteins. *J Mol Biol* 48, 443-453 (1970).

The invention claimed is:

1. A method for treating psoriasis, said method comprising a step of administering a hepcidin antagonist to a patient in need thereof, wherein said hepcidin antagonist is administered topically to the skin, and wherein said hepcidin antagonist is selected from the group consisting of anti-hepcidin antibodies, anti-hepcidin aptamers, lexaptepid pegol, the PRS-080 compound and an antisense oligonucleotide targeting the hepcidin gene, wherein the anti-hepcidin aptamer is a peptide aptamer having an anti-hepcidin antibody variable region and wherein the antisense oligonucleotide comprises a sequence that is complementary to a region of hepcidin mRNA.

2. The method according to claim 1, wherein the hepcidin antagonist is administered in an amount sufficient to inhibit and/or reduce neutrophil migration.

* * * * *